United States Patent [19]

Dean et al.

[11] Patent Number: 4,822,453

[45] Date of Patent: Apr. 18, 1989

[54] ABSORBENT STRUCTURE CONTAINING INDIVIDUALIZED, CROSSLINKED FIBERS

[75] Inventors: Walter L. Dean, Memphis; Danny R. Moore, Germantown; James W. Owens; Howard L. Schoggen, both of Memphis, all of Tenn.

[73] Assignee: The Procter & Gamble Cellulose Company, Memphis, Tenn.

[21] Appl. No.: 879,708

[22] Filed: Jun. 27, 1986

[51] Int. Cl.$^4$ ............................................. D21H 5/12
[52] U.S. Cl. .................................. 162/157.6; 162/158; 162/182; 604/375
[58] Field of Search ............... 162/9, 100, 157.6, 182, 162/158; 604/375

[56] References Cited

U.S. PATENT DOCUMENTS

| | | | |
|---|---|---|---|
| 3,046,079 | 7/1962 | Reeves et al. | 8/116.4 |
| 3,069,311 | 12/1962 | Harpham et al. | 162/157.6 |
| 3,224,926 | 12/1965 | Bernardin | 162/146 |
| 3,241,553 | 3/1966 | Steiger | 128/156 |
| 3,434,918 | 3/1969 | Bernardin | 162/111 |
| 3,440,135 | 4/1969 | Chung | 162/157 |
| 3,455,778 | 7/1969 | Bernardin | 162/113 |
| 3,756,913 | 9/1973 | Wodka | 162/183 |
| 3,819,470 | 6/1974 | Shaw et al. | 162/157 |
| 3,932,209 | 1/1976 | Chatterjee | 162/157 |
| 4,035,147 | 7/1977 | Sangenis et al. | 8/116.4 |
| 4,204,054 | 5/1980 | Lesas et al. | 536/56 |
| 4,689,118 | 8/1987 | Makoui et al. | 162/100 |

FOREIGN PATENT DOCUMENTS

| | | | |
|---|---|---|---|
| 993618 | 7/1976 | Canada | 19/2 |
| 0122042 | 10/1984 | European Pat. Off. | |

Primary Examiner—Peter Chin
Attorney, Agent, or Firm—Bart S. Hersko; Thomas J. Slone; Leonard W. Lewis

[57] ABSTRACT

Absorbent structures containing individualized, crosslinked fibers. The individualized, crosslinked fibers preferably have between about 0.5 mole % and about 3.5 mole % crosslinking agent, calculated on a cellulose anhydroglucose molar basis, reacted with the fibers in the form of intrafiber crosslink bonds, wherein the crosslinking agent is selected from the group consisting of $C_2$–$C_8$ dialdehydes, $C_2$–$C_8$ dialdehyde acid analogues having at least one aldehyde functionality, and oligomers of such $C_2$–$C_8$ dialdehydes and dialdehyde acid analogues. More preferably, the crosslinking agent is glutaraldehyde, and between about 0.75 mole % and about 2.5 mole % crosslinking agent react to form the intrafiber crosslink bonds. Also preferably, the absorbent structures have actual dry densities greater than their corresponding equilibrium wet densities, and expand upon wetting. The absorbent structures may also contain hydrogel-forming material.

32 Claims, No Drawings

ABSORBENT STRUCTURE CONTAINING INDIVIDUALIZED, CROSSLINKED FIBERS

FIELD OF THE INVENTION

This invention is concerned with cellulosic fibers having high fluid absorption properties, and especially with absorbent structures made from such cellulosic fibers. More specifically, this invention is concerned with absorbent structures containing individualized, crosslinked, cellulosic fibers.

BACKGROUND OF THE INVENTION

Fibers crosslinked in substantially individualized form and various methods for making such fibers have been described in the art. The term "individualized, crosslinked fibers" refers to cellulosic fibers that have primarily intrafiber chemical crosslink bonds. That is, the crosslink bonds are primarily between cellulose molecules of single fiber, rather than between cellulose molecules of separate fibers. Individualized, crosslinked fibers are generally regarded as being useful in absorbent product applications. In general, three categories of processes have been reported for making individualized, crosslinked fibers. These processes, described below, are herein referred to as (1) dry crosslinking processes, (2) aqueous solution crosslinking processes, and (3) substantially non-aqueous solution crosslinking processes. The fibers themselves and absorbent structures containing individualizes, crosslinked fibers generally exhibit an improvement in at least one significant absorbency property relative to conventional, uncrosslinked fibers. Often, this improvement in absorbency is reported in terms of absorbent capacity. Additionally, absorbent structures made from individualized crosslinked fibers generally exhibit increased wet resilience and increased dry resilience relative to absorbent structures made from uncrosslinked fibers. The term "resilience" shall hereinafter refer to the ability of pads made from cellulosic fibers to return toward an expanded original state upon release of a compressional force. Dry resilience specifically refers to the ability of an absorbent structure to expand upon release of compressional force applied while the fibers are in a substantially dry condition. Wet resilience specifically refers to the ability of an absorbent structure to expand upon release of compressional force applied while the fibers are in a moistened condition. For the purposes of this invention and consistency of disclosure, wet resilience shall be observed and reported for an absorbent structure moistened to saturation.

Processes for making individualized, crosslinked fibers with dry crosslinking technology are described in U.S. Pat. No. 3,224,926 issued to L. J. Bernardin on Dec. 21, 1965. Individualized, crosslinked fibers are produced by impregnating swollen fibers in an aqueous solution with crosslinking agent, dewatering and defiberizing the fibers by mechanical action, and drying the fibers at elevated temperature to effect crosslinking while the fibers are in a substantially individual state. The fibers are inherently crosslinked in an unswollen, collapsed state as a result of being dehydrated prior to crosslinking. Processes as exemplified in U.S. Pat. Nos. 3,224,926, wherein crosslinking is caused to occur while the fibers are in an unswollen, collapsed state, are referred to as processes for making "dry crosslinked" fibers. Dry crosslinked fibers are characterized by low fluid retention values (FRV). It is suggested in U.S. Pat. No. 3,440,135, issued to R. Chung on Apr. 22, 1969, to soak the fibers in an aqueous solution of a crosslinking agent to reduce interfiber bonding capacity prior to carrying out a dry crosslinking operation similar to that described in U.S. Pat. No. 3,224,926. This time consuming pretreatment, preferably between about 16 and 48 hours, is alleged to improve product quality by reducing nit content resulting from incomplete defibration.

Processes for producing aqueous solution crosslinked fibers are disclosed, for example, in U.S. Pat. No. 3,421,553, issued to F. H. Steiger Mar. 22, 1966. Individualized, crosslinked fibers are produced by crosslinking the fibers in an aqueous solution containing a crosslinking agent and a catalyst. Fibers produced in this manner are hereinafter referred to as "aqueous solution crosslinked" fibers. Due to the swelling effect of water on cellulosic fibers, aqueous solution crosslinked fibers are crosslinked while in an uncollapsed, swollen state. Relative to dry crosslinked fibers, aqueous solution crosslinked fibers as disclosed in U.S. Pat. No. 3,421,553 have greater flexibility and less stiffness, and are characterized by higher fluid retention value (FRV). Absorbent structures made from aqueous solution crosslinked fibers exhibit lower wet and dry resilient than pads made from dry crosslinked fibers.

In U.S. Pat. No. 4,035,147, issued to S. Sangenis, G. Guiroy and J. Quere on July 12, 1977, a method is disclosed for producing individualized, crosslinked fibers by contacting dehydrated, nonswollen fibers with crosslinking agent and catalyst in a substantially nonaqueous solution which contains an insufficient amount of water to cause the fibers to swell. Crosslinking occurs while the fibers are in this substantially nonaqueous solution. This type of process shall hereinafter be referred to as a nonaqueous solution crosslinked process; and the fibers thereby produced, shall be referred to as nonaqueous solution crosslinked fibers. The nonaqueous solution crosslinked fibers disclosed in U.S. Pat. No. 4,035,147 do not swell even upon extended contact with solutions known to those skilled in the art as swelling reagents. Like dry crosslinked fibers, they are highly stiffened by crosslink bonds, and absorbent structures made therefrom exhibit relatively high wet and dry resilience.

Crosslinked fibers as described above are believed to be useful for lower density absorbent product applications such as diapers and also higher density absorbent product applications such as catamenials. However, such fibers have not provided sufficient absorbency benefits, in view of their detriments and costs, over conventional fibers to result in significant commercial success. Commercial appeal of crosslinked fibers has also suffered due to safety concerns. The most widely referred to crosslinking agent in the literature, formaldehyde, unfortunately causes irritation in human skin and has been associated with other human safety concerns. Removal of free formaldehyde to sufficiently low levels in the crosslinked product such that irritation to skin and other human safety concerns are avoided has been hindered by both technical and economic barriers.

Aqueous solution crosslinked fibers, while useful for certain higher density absorbent pad applications such as surgical dressings, tampons and sanitary napkins wherein densities ordinarily are about 0.40 g/cc, are excessively flexible when in a wet state and therefore result in absorbent structures which have low wet resilience. Furthermore, upon wetting, aqueous solution crosslinked fibers become too flexible to structurally support the pad at lower fiber densities. The wetted pad therefore collapses and absorbent capacity is reduced.

Dry crosslinked fibers and nonaqueous solution crosslinked fibers, have generally resulted in fibers of excessive stiffness and dry resiliency, thereby making them difficult to form into densified sheets for transport and subsequently refluff without fiber damage. Furthermore, when compressed in a dry state, pads made from these fibers have exhibited a low responsiveness to wetting. That is, once compressed in a dry state, they have not shown the ability to regain substantial amounts of their prior absorbent capacity upon wetting.

Another difficulty which has been experienced with respect to dry and nonaqueous solution crosslinked fibers is that the fibers rapidly flocculate upon wet-laying on a foraminous forming wire. This has hindered formation of absorbent wet laid structures as well as formation of densified sheets which would facilitate economic transport of the fibers to a converting plant.

A further difficulty which has been experienced with respect to dry and nonaqueous solution crosslinked fibers is that while pads made form such fibers exhibit high wicking and absorbent capacity, such pads in actual use have also resulted in higher levels of moisture on wearer skin surfaces relative to pads made from conventional fibers.

It is an object of this invention to provide individualized, crosslinked fibers and absorbent structures made from such fibers wherein the absorbent structures made form the crosslinked fibers have high levels of absorbency relative to absorbent structures made from uncrosslinked fibers, exhibit higher wet resilience and lower dry resilience than structures made from prior known dry crosslinked and nonaqueous solution crosslinked fibers, and exhibit higher wet resilience and structural integrity than structures made from prior known aqueous solution crosslinked fibers.

It is a further object of this invention to provide individualized, crosslinked fibers and absorbent structures made from such fibers, as described above, which have improved responsiveness to wetting relative to prior known crosslinked fibers and conventional, uncrosslinked fibers.

It is additionally an object of this invention to provide commercially viable individualized crosslinked fibers and absorbent structures made from such fibers, as described above, which can be safely utilized in the vicinity of human skin.

It is another object of this invention to provide absorbent structures having improved absorbent capacity and wicking which, in actual use, provide high levels of wearer skin dryness.

SUMMARY OF THE INVENTION

It has been found that the objects identified above, and other objects as may become apparent, may be med by individualized, crosslinked fibers and incorporation of these fibers into absorbent structures, as disclosed herein. Preferably, the individualized, crosslinked fibers have between about 0.5 mole % and about 2.5 mole % crosslinking agent, calculated on a cellulose anhydroglucose molar basis, reacted with the fibers in the form of intrafiber crosslink bonds wherein the crosslinking agent is selected from the group consisting of $C_2$–$C_8$ dialdehydes, $C_2$–$C_8$ dialdehyde acid analogues having at least one aldehyde functionality, and oligomers of such $C_2$–$C_8$ dialdehydes and dialdehyde acid analogues. Such fibers, which are characterized by having water retention values (WRV's) of less than about 60, have been found to fulfill the identified objects relating to individualized, crosslinked fibers and provide unexpectedly good absorbent performance in absorbent structure applications.

The individualized, crosslinked fibers are, without limiting the scope of the invention, preferably formed into compressed absorbent structures that expand upon wetting, or into lower density absorbent structures which preferably substantially maintain constant volume upon wetting.

The absorbent structures may additionally contain hydrogel-forming material. Significantly improved skin dryness and absorbent capacity and skin dryness of the wearer may be obtained with the utilization of hydrogel-forming material with individualized, crosslinked fibers. Significantly improved wicking and absorbent capacity are obtained by utilizing individualized, crosslinked fibers with hydrogel-forming material relative to utilizing conventional, uncrosslinked cellulose fibers with hydrogel-forming material. Surprisingly, such improved results may be obtained pursuant to the utilization of lower levels of hydrogel-forming material, calculated weight basis, for individualized, crosslinked fiber-containing pads compared to conventional cellulosic fibers pads.

DETAILED DESCRIPTION OF THE INVENTION

Cellulosic fibers of diverse natural origin are applicable to the invention. Digested fibers from softwood, hardwood or cotton linters are preferably utilized. Fibers from Esparto grass, bagasse, kemp, flax, and other lignaceous and cellulosic fiber sources may also be utilized as raw material in the invention. The fibers may be supplied in slurry, unsheeted or sheeted form. Fibers supplied as wet lap, dry lap or other sheeted form are preferably rendered into unsheeted form by mechanically disintegrating the sheet, preferably prior to contacting the fibers with the crosslinking agent. Also, preferably the fibers are provided in a wet or moistened condition. Most preferably, the fibers are never-dried fibers. In the case of dry lap, it is advantageous to moisten the fibers prior to mechanical disintegration in order to minimize damage to the fibers.

The optimum fiber source utilized in conjunction with this invention will depend upon the particular end use contemplated. Generally, pulp fibers made by chemical pulping processes are preferred. Completely bleached, partially bleached and unbleached fibers are applicable. It may frequently be desired to utilize bleached pulp for its superior brightness and consumer appeal. In one novel embodiment of the invention, hereinafter more fully described, the fibers are partially bleached, crosslinked, and then bleached to completion. For products such as paper towels and absorbent pads for diapers, sanitary napkins, catamenials, and other similar absorbent paper products, it is especially preferred to utilize fibers from southern softwood pulp due to their premium absorbency characteristics.

Preferred crosslinking agents applicable to the present development include $C_2$–$C_8$ dialdehydes, as well as acid analogues of such dialdehydes wherein the acid analogue has at least one aldehyde group, and oligomers of such dialdehydes and acid analogues. These compounds are capable of reacting with at least two hydroxyl groups in a single cellulose chain or on proximately located cellulose chains in a single fiber. Those knowledgeable in the area of crosslinking agents will recognize that the dialdehyde crosslinking agents described above will be present, or may react in a variety of forms, including the acid analogue and oligomer forms identified above. All such forms are meant to be included within the scope of the invention. Reference to a particular crosslinking agent shall therefore hereinafter refer to that particular crosslinking agent as well as other forms as may be present in an aqueous solution. Particular crosslinking agents contemplated for use with the invention are glutaraldehyde, glyoxal, and glyoxylic acid. Glutaraldehyde is especially preferred, since it has provided fibers with the highest levels of absorbency and resiliency, is believed to be safe and non-irritating to human skin when in a reached, crosslinked condition, and has provided the most stable, crosslink bonds. Monoaldehydic compounds not having an additional carboxylic group, such as acetaldehyde and furfural, have not been found to provide absorbent structures with the desired levels of absorbent capacity, resilience, and responsiveness to wetting.

It has been unexpectedly discovered that superior absorbent pad performance may be obtained at crosslinking levels which are substantially lower than crosslinking levels previously practiced. In general, unexpectedly good results are obtained for absorbent pads made from individualized, crosslinked fibers having between about 0.5 mole % and about 3.5 mole % crosslinking agent, calculated on a cellulose anhydroglucose molar basis, reacted with the fibers.

Preferably, the crosslinking agent is contacted with the fibers in a liquid medium, under such conditions that the crosslinking agent penetrated into the interior of the individual fiber structures. However, other methods of crosslinking agent treatment, including spraying of the fibers while in individualized, fluffed form, are also within the scope of the invention.

Generally, the fibers will also be contacted with an appropriate catalyst prior to crosslinking. The type, amount, and method of contact of catalyst to the fibers will be dependent upon the particular crosslinking process practiced. These variables will be discussed in more detail below.

Once the fibers are treated with crosslinking agent and catalyst, the crosslinking agent is caused to react with the fibers in the substantial absence of interfiber bonds, i.e., while interfiber contact is maintained at a low degree of occurrence relative to unfluffed pulp fibers, or the fibers are submerged in a solution that does not facilitate the formation of interfiber bonding, especially hydrogen bonding. This result sin the formation of crosslink bonds which are intrafiber in nature. Under these conditions, the crosslinking agent reacts to form crosslink bonds between hydroxyl groups of a single cellulose chain or between hydroxyl groups of proximately located cellulose chains of a single cellulosic fiber.

Although not presented or intended to limit the scope of the invention, it is believed that the crosslinking agent reacts with the hydroxyl groups of the cellulose to form hemiacetal and acetal bonds. The formation of acetal bonds, believed to be the desirable bond types providing stable crosslink bonds, if favored under acidic reaction conditions. Therefore, acid catalyzed crosslinking conditions are highly preferred for the purposes of this invention.

The fibers are preferably mechanically defibrated into a low density individualized fibrous form known as "fluff" prior to reaction of the crosslinking agent with the fibers. Mechanical defibration may be performed by a variety of methods which are presently known in the art or which may hereinafter become known. Mechanical defibration is preferably performed by a method wherein knot formation and fiber damage are minimized. One type of device which has been found to be particularly useful for defibration the cellulosic fibers is the three stage fluffing device described in U.S. Pat. No. 3,987,968, issued to D. R. Moore and O. A. Shields on Oct. 26, 1976, said patent being hereby expressly incorporated by reference into this disclosure. The fluffing device described in U.S. Pat. No. 3,987,968 subjects moist cellulosic pulp fibers to a combination of mechanical impact, mechanical agitation, air agitation and a limited amount of air drying to create a substantially knot-free fluff. The individualized fibers have imparted thereto an enhanced degree of curl and twist relative to the amount of curl and twist naturally present in such fibers. It is believed that this additional curl and twist enhances the resilient character of absorbent structures made from the finished, crosslinked fibers.

Other applicable methods for defibrating the cellulosic fibers include, but are not limited to, treatment with a Waring blender and tangentially contacting the fibers with a rotating disk refiner or wire brush. Preferably, an air stream is directed toward the fibers during such defibration to aid in separating the fibers into substantially individual form.

Regardless of the particular mechanical device used to form the fluff, the fibers are preferably mechanically treated while initially containing at least abut 20% moisture, and preferably containing between about 40% and about 60% moisture.

Mechanical refining of fibers at high consistency or of partially dried fibers may also be utilized to provide curl or twist to the fibers in addition to curl or twist imparted as a result of mechanical defibration.

The fibers made according to the present invention have unique combinations of stiffness and resiliency, which allow absorbent structures made from the fibers to maintain high levels of absorptivity, and exhibit high levels of resiliency and an expansionary responsiveness to wetting of a dry, compressed absorbent structure. In addition to having the levels of crosslinking within the stated ranges, the crosslinked fibers are characterized by having water retention values (WRV's) of less than about 60, and preferably between about 28 and 45, for conventional, chemically pulped, papermaking fibers. The WRV of a particular fiber is indicative of the level of crosslinking and the degree of swelling of the fiber at the time of crosslinking. Those skilled in the art will recognize that the more swollen a fiber is at the time of crosslinking, the higher the WRV will be for a given level of crosslinking. Very highly crosslinked fibers, such as those produced by the prior known dry crosslinking processes previously discussed, have been found to have WRV's of less than about 25, and generally less than about 20. The particular crosslinking process utilized will, of course, affect the WRV of the crosslinked fiber. However, any process which will result in crosslinking levels and WRV's within the stated limits is believed to be, and is intended to be, within the scope of this invention. Applicable methods of crosslinking include dry crosslinking processes and nonaqueous solution crosslinking processes as generally discussed in the Background Of The Invention. Certain preferred dry crosslinking and nonaqueous solution crosslinking processes, within the scope of the present invention, will be discussed in more detail below. Aqueous solution crosslinking processes wherein the solution causes the fibers to become highly swollen will result in fibers having WRV's which are in excess of about 60. These fibers will provide insufficient stiffness and resiliency for the purposes of the present invention.

Specifically referring to dry crosslinking processes, individualized, crosslinked fibers may be produced from such a process by providing a quantity of cellulosic fibers, contacting a slurry of the fibers with a type and amount of crosslinking agent as described above, mechanically separating, e.g., defibrating the fibers into substantially individual form, and drying the fibers and causing the crosslinking agent to react with the fibers in the presence of a catalyst to form crosslink bonds while the fibers are maintained in substantially individual form. The defibration step, apart from the drying step, is believed to impart additional curl. Subsequent drying is accompanied by twisting of the fibers, with the degree of twist being enhanced by the curled geometry of the fiber. As used herein, fiber "curl" refers to a geometric curvature of the fiber about the longitudinal axis of the fiber. "Twist" refers to a rotation of the fiber about the perpendicular cross-section of the longitudinal axis of the fiber. For exemplary purposes only, and without intending to specifically limit the scope of the invention, individualized, crosslinked fibers within the scope of the invention having an average level of about 6 (six) twists per millimeter of fiber have been observed.

Maintaining the fibers in substantially individual form during drying and crosslinking allows the fibers to twist during drying and thereby be crosslinked in such twisted, curled state. Drying fibers under such conditions that the fibers may twist and curl is referred to as drying the fibers under substantially unrestrained conditions. On the other hand, drying fibers in sheeted form results in dried fibers which are not twisted and curled as fibers dried in substantially individualized form. It is believed that interfiber hydrogen bonding "restrains" the relative occurrence of twisting and curling of the fiber.

There are various methods by which the fibers may be contacted with the crosslinking agent and catalyst. In one embodiment, the fibers are contacted with a solution which initially contains both the crosslinking agent and the catalyst. In another embodiment, the fibers are contacted with an aqueous solution of crosslinking agent and allowed to soak prior to addition of the catalyst. The catalyst is subsequently added. In a third embodiment, the crosslinking agent and catalyst are added to an aqueous slurry of the cellulosic fibers. Other methods in addition to those described herein will be apparent to those skilled in the art, and are intended to be included within the scope of this invention. Regardless of the particular method by which the fibers are contacted with crosslinking agent and catalyst, the cellulosic fibers, crosslinking agent and catalyst are preferably mixed and/or allowed to soak sufficiently with the fibers to assure thorough contact with and impregnation of the individual fibers.

In general, any substance which catalyzes the crosslinking mechanism may be utilized. Applicable catalyst include organic acids and acid salts. Especially preferred catalysts are salts such as aluminum, magnesium, zinc and calcium salts of chlorides nitrates or sulfates. One specific example of a preferred salt is zinc nitrate hexahydrate. Other catalysts include acids such as sulfuric acid, hydrochloric acid and other mineral and organic acids. The selected catalyst may be utilized as the sole catalyzing agent, or in combination with one or more other catalysts. It is believed that combinations of acid salts and organic acids as catalyzing agents provide superior crosslinking reaction efficiency. Unexpectedly high levels of reaction completion have been observed for catalyst combinations of zinc nitrate salts and organic acids, such as citric acid, and the use of such combinations is preferred. Mineral acids are useful for adjusting pH of the fibers while being contacted with the crosslinking agent in solution, but are preferably not utilized as the primary catalyst.

The optimum amount of crosslinking agent and catalyst utilized will depend upon the particular crosslinking agent utilized, the reaction conditions and the particular product application contemplated.

The amount of catalyst preferably utilized is, of course, dependent upon the particular type and amount of crosslinking agent and the reaction conditions, especially temperature and pH. In general, based upon technical and economic considerations, catalyst levels of between about 10 wt. % and about 60 wt. %, based on the weight of crosslinking agent added to the cellulosic fibers, are preferred. For exemplary purposes, in the case wherein the catalyst utilized is zinc nitrate hexahydrate and the crosslinking agent is glutaraldehyde, a catalyst level of about 30 wt. %, based upon the amount of glutaraldehyde added, is preferred. Most preferably, between about 5% and about 30%, based upon the weight of the glutaraldehyde, of an organic acid, such as citric acid, is also added as a catalyst. It is additionally desirable to adjust the aqueous portion of the cellulosic fiber slurry or crosslinking agent solution to a target pH of between about pH 2 and about pH 5, more preferably between about pH 2.5 and about pH 3.5, during the period of contact between the crosslinking agent and the fibers.

The cellulosic fibers should generally be dewatered and optionally dried. The workable and optimal consistencies will vary depending upon the type of fluffing equipment utilized. In the preferred embodiments, the cellulosic fibers are dewatered and optimally dried to a consistency of between about 30% and about 80%. More preferably, the fibers are dewatered and dried to a consistency level of between about 40% and about 60%. Drying the fibers to within these preferred ranges generally will facilitate defibration of the fibers into individualized form without excessive formation of knots associated with higher moisture levels and without high levels of fiber damage associated with lower moisture levels.

For exemplary purposes, dewatering may be accomplished by such methods as mechanically pressing, centrifuging, or air drying the pulp. Additional drying is preferably performed by such methods, known in the art as air drying or flash drying, under conditions such that the utilization of high temperature for an extended period of time is not required. Excessively high temperature at this stage of the process may result in the premature initiation of crosslinking. Preferably, temperatures in excess of about 160° C. are not maintained for periods of time in excess of 2 to 3 seconds. Mechanical defibration is performed as previously described.

The defibrated fibers are then heated to a suitable temperature for an effective period of time to cause the crosslinking agent to cure, i.e., to react with the cellulosic fibers. The rate and degree of crosslinking depends upon dryness of the fibers, temperature, amount and type of catalyst and crosslinking agent and the method utilized for heating and/or drying the fibers while crosslinking is performed. Crosslinking at a particular temperature will occur at a higher rate for fibers of a certain initial moisture content when accompanied by a continuous air through drying than when subjected to drying/heating in a static oven. Those skilled in the art will recognize that a number of temperature-time relationships exist for the curing of the crosslinking agent. Conventional paper drying temperatures, (e.g., 120° F. to about 150° F.), for periods of between about 30 minutes and 60 minutes, under static, atmospheric conditions will generally provide acceptable curing efficiencies for fibers having moisture contents less than about 5%. Those skilled in the art will also appreciate that higher temperatures and air convection decrease the time required for curing. However, curing temperatures are preferably maintained at less than about 160° C., since exposure of the fibers to such high temperatures in excess of about 160° C. may lead to yellowing or other damaging of the fibers.

The maximum level of crosslinking will be achieved when the fibers are essentially dry (having less than about 5% moisture). Due to this absence of water, the fibers are crosslinked while in a substantially unswollen, collapsed state. Consequently, they characteristically have low fluid retention values (FRV) relative to the range applicable to this invention. The FRV refers to the amount of fluid calculated on a dry fiber basis, that remains absorbed by a sample of fibers that have been soaked and then centrifuged to remove interfiber fluid. (The FRV is further defined and the Procedure For Determining FRV, is described below.) The amount of fluid that the crosslinked fibers can absorb is dependent upon their ability to swell upon saturation or, in other words, upon their interior diameter or volume upon swelling to a maximum level. This, in turn, is dependent upon the level of crosslinking. As the level of intrafiber crosslinking increases for a given fiber and process, the FRV of the fiber will decrease until the fiber does not swell at all upon wetting. Thus, the FRV value of a fiber is structurally descriptive of the physical condition of the fiber at saturation. Unless otherwise expressly indicated, FRV data described herein shall be reported in terms of the water retention value (WRV) of the fibers. Other fluids, such as salt water and synthetic urine, may also be advantageously utilized as a fluid medium for analysis. Generally, the FRV of a particular fiber crosslinked by procedures wherein curing is largely dependent upon drying, such as the present process, will be primarily dependent upon the crosslinking agent and the level of crosslinking. The WRV's of fibers crosslinked by this dry crosslinking process at crosslinking agent levels applicable to this invention are generally less than about 50, greater than about 25, and are preferably between about 28 and about 45. Bleached SSK fibers having between about 0.5 mole % and about 2.5 mole % glutaraldehyde reacted thereon, calculated on a cellulose anhydroglucose molar basis, have been observed to have WRV's respectively ranging from about 40 to about 28. The degree of bleaching and the practice of post-crosslinking bleaching steps have been found to affect WRV. This effect will be explored in more detail below. Southern softwood Kraft (SSK) fibers prepared by dry crosslinking processes known prior to the present invention, have levels of crosslinking higher than described herein, and have WRV's less than about 25. Such fibers, as previously discussed, have been observed to be exceedingly stiff and to exhibit lower absorbent capabilities than the fibers of the present invention.

In another process for making individualized, crosslinked fibers by a dry crosslinking process, cellulosic fibers are contacted with a solution containing a crosslinking agent as described above. Either before or after being contacted with the crosslinking agent, the fibers are provided in a sheet form. Preferably, the solution containing the crosslinking agent also contains one of the catalysts applicable to dry crosslinking processes, also described above. The fibers, while in sheeted form, are dried and caused to crosslink preferably by heating the fibers to a temperature of between about 120° C. and about 160° C. Subsequent to crosslinking, the fibers are mechanically separated into substantially individual form. This is preferably performed by treatment with a fiber fluffing apparatus such as the one described in U.S. Pat. No. 3,987,968 or may be performed with other methods for defibrating fibers as may be known in the art. The individualized, crosslinked fibers made according to this sheet crosslinking process are treated with a sufficient amount of crosslinking agent such that between about 0.5 mole % and about 3.5 moles 5 crosslinking agent, calculated on a cellulose anhydroglucose molar basis and measured subsequent to defibration are reacted with the fibers in the form of intrafiber crosslink bonds. Another effect of drying and crosslinking the fibers while in sheet form is that fiber to fiber bonding restrains the fibers from twisting and curling with increased drying. Compared to individualized, crosslinked fibers made according to a process wherein the fibers are dried under substantially unrestrained conditions and subsequently crosslinked in a twisted, curled configuration, absorbent structures made the relatively untwisted fibers made the sheet curing process described above would be expected to exhibit lower wet resiliency and lower responsiveness to wetting of a dry absorbent structure.

Another category of crosslinking processes applicable to the present invention is nonaqueous solution cure crosslinking processes. The same types of fibers applicable to dry crosslinking processes may be used in the production of nonaqueous solution crosslinked fibers. The fibers are treated with a sufficient amount of crosslinking agent such that between about 0.5 mole % and about 3.5 mole % crosslinking agent subsequently react with the fibers, wherein the level of crosslinking agent reacted is calculated subsequent to said crosslinking reaction, and with an appropriate catalyst. The crosslinking agent is caused to react while the fibers are submerged in a solution which does not include any substantial levels of swelling of the fibers. The fibers, however may contain up to about 30% water, or be otherwise swollen in the crosslinking solution to a degree equivalent to fibers having about a 30% moisture content. Such partially swollen fiber geometry has been found to provide additional unexpected benefits as hereinafter more fully discussed. The crosslinking solution contains a nonaqueous, water-miscible, polar diluent such as, but not limited to, acetic acid, propanoic acid, or acetone. Preferred catalysts include mineral acids, such as sulfuric acid, and halogen acids, such as hydrochloric acid. Other applicable catalysts include salts of mineral acids and halogen acids organic acids and salts thereof. Crosslinking solution systems applicable for use as a crosslinking medium also include those disclosed in U.S. Pat. No. 4,035,147, issued to S. Sangenis, G. Guiroy, and J. Quere, on July 12, 1977, which is hereby incorporated by reference into this disclosure. The crosslinking solution may include some water or other fiber swelling liquid, however, the amount of water is preferably insufficient to cause a level of swelling corresponding to that incurred by 70% consistency pulp fibers (30% aqueous moisture content). Additionally, crosslinking solution water contents less than about 10% of the total volume of the solution, exclusive of the fibers are preferred. Levels of water in the crosslinking solution in excess of this amount decrease the efficiency and rate of crosslinking.

Absorption of crosslinking agent by the fibers may be accomplished in the crosslinking solution itself or in a prior treatment stage including, but not limited to, saturation of the fibers with either an aqueous or nonaqueous solution containing the crosslinking agent. Preferably, the fibers are mechanically defibrated into individual form. This mechanical treatment may be performed by methods previously described for fluffing fibers in connection with the previously described dry crosslinking process.

It is especially preferred to include in the production of fluff a mechanical treatment which causes the moist cellulosic fibers to assume a curled or twisted condition to a degree in excess of the amount of curl or twist, if any, of the natural state of the fibers. This can be accomplished by initially providing fibers for fluffing which are in a moist state, subjecting the fibers to a mechanical treatment such as those previously described methods for defibrating the fibers into substantially individual form, and at least partially drying the fibers.

The relative amounts of curl and twist imparted to the fibers is in part dependent upon the moisture content of the fibers. Without limiting the scope of the invention, it is believed that the fibers naturally twist upon drying under conditions wherein fiber to fiber contact is low, i.e., when the fibers are in an individualized form. Also, mechanical treatment of moist fibers initially causes the fibers to become curled. When the fibers are then dried or partially dried under substantially unrestrained conditions, they become twisted with the degree of twist being enhanced by the additional amount of curl mechanically imparted. The defibration fluffing steps are preferably practiced on high consistency moist pulp or pulp which has been dewatered to fiber consistency of about 45% to about 55% (determined prior to initialization of defibration).

Subsequent to defibration, the fibers should be dried to between 0% and about 30% moisture content prior to being contacted with the crosslinking solution, if the defibration step has not already provided fibers having moisture contents within that range. The drying step should be performed while the fibers are under substantially unrestrained conditions. That is, fiber to fiber contact should be minimized so that the twisting of the fibers inherent during drying is not inhibited. Both a drying and flash drying methods are suitable for this purpose.

The individualized fibers are next contacted with a crosslinking solution which contains a water-miscible, nonaqueous diluent, a crosslinking agent and a catalyst. The crosslinking solution may contain a limited amount of water. The water content of the crosslinking solution should be less than about 18% and is preferably less than about 9%.

A bat of fibers which have not been mechanically defibrated may also be contacted with a crosslinking solution as described above.

The amounts of crosslinking agent and acid catalyst utilized will depend upon such reaction conditions as consistency, temperature, water content in the crosslinking solution and fibers, type of crosslinking agent and diluent in the crosslinking solution, and the amount of crosslinking desired. Preferably, the amount of crosslinking agent utilized ranges from about 0.2 wt. % to about 10 wt % (based upon the total, fiber-free weight of the crosslinking solution). Preferred acid catalyst content is additionally dependent upon the acidity of the catalyst in the crosslinking solution. Good results may generally be obtained for catalyst content, including hydrochloric acid, between about 0.3 wt % and about 5 wt % (fiber-free crosslinking solution weight basis) in crosslinking solutions containing an acetic acid diluent, preferred levels of glutaraldehyde, and a limited amount of water. Slurries of fibers and crosslinking solution having fiber consistencies of less than about 10 wt % are preferred for crosslinking in conjunction with the crosslinking solutions described above.

The crosslinking reaction may be carried out at ambient temperatures or, for accelerated reaction rates, at elevated temperatures preferably less than about 40° C.

There are a variety of methods by which the fibers may be contacted with, and crosslinked in, the crosslinking solution. In one embodiment, the fibers are contacted with the solution which initially contains both the crosslinking agent and the acid catalyst. The fibers are allowed to soak in the crosslinking solution, during which time crosslinking occurs. In another embodiment, the fibers are contacted with the diluent and allowed to soak prior to addition of the acid catalyst. The acid catalyst subsequently is added, at which time crosslinking begins. Other methods in addition to those described will be apparent to those skilled in the art, and are intended to be within the scope of this invention.

Preferably, the crosslinking agent and the conditions at which crosslinking is performed are chosen to facilitate intrafiber crosslinking. Thus, it is advantageous for the crosslinking reaction to occur in substantial part after the crosslinking agent has had sufficient time to penetrate into the fibers. Reaction conditions are preferably chosen so as to avoid instantaneous crosslinking unless the crosslinking agent has already penetrated into the fibers. Periods of reaction during which time crosslinking is substantially completed over a period of about 30 minutes are preferred. Longer reaction periods are believed to provide minimal marginal benefit in fiber performance. However, both shorter periods, including substantially instantaneous crosslinking, and longer periods are meant to be within the scope of this invention.

It is also contemplated to only partially cure while in solution, and subsequently complete the crosslinking reaction later in the process by drying or heating treatments.

Following the crosslinking step, the fibers are drained and washed. Preferably, a sufficient amount of a basic substance such as caustic is added in the washing step to neutralize any acid remaining in the pulp. After washing, the fibers are defluidized and dried to completion. Preferably, the fibers are subjected to a second mechanical defibration step which causes the crosslinked fibers to curl, e.g., fluffing by defibration, between the defluidizing and drying steps. Upon drying, the curled condition of the fibers imparts additional twist as previously described in connection with the curling treatment prior to contact with the crosslinking solution. The same apparatuses and methods for inducing twist and curl described in connection with the first mechanical defibration step are applicable to this second mechanical defibration step. As used herein, the term "defibration" shall refer to any of the procedures which may be used to mechanically separate the fibers into substantially individual form, even though the fibers may already be provided in such form. "Defibration" therefore refers to the step of mechanically treating the fibers, in either individual form or in a more compacted form, to a mechanical treatment step which (a) would separate the fibers into substantially individual form if they were not already in such form, and (b) imparts curl and twist to the fibers upon drying.

This second defibration treatment, after the fibers have been crosslinked, has been found to increase the twisted, curled character of the pump. This increase in the twisted, curled configuration of the fibers leads to enhanced absorbent structure resiliency and responsiveness to wetting. A second defibration treatment may be practiced upon any of the crosslinked fibers described herein which are in a moist condition. However, it is a particular advantage of the nonaqueous solution crosslinking method that a second defibration step is possible without necessitating an additional drying step. This is due to the fact that the solution in which the fibers are crosslinked keep the fibers flexible subsequent to crosslinking even though not causing the fibers to assume an undesirable, highly swollen state.

It has been further unexpectedly found that increased degrees of absorbent structure expansion upon wetting compressed pads can be obtained for structures made from fibers which have been crosslinked while in a condition which is twisted but partially swollen relative to fibers which have been thoroughly dried of water prior to crosslinking.

Improved results are obtained for individualized, crosslinked fibers which have been crosslinked under conditions wherein the fibers are dried to between about 18% and about 30% water content prior to contact with the crosslinking solution. In the case wherein a fiber is dried to completion prior to being contacted with the crosslinking solution, it is in a non-swollen, collapsed state. The fiber does not become swollen upon contact with the crosslinking solution due to the low water content of the solution. As discussed before, a critical aspect of the crosslinking solution is that is does not cause any substantial swelling of the fibers. However, when the diluent of the crosslinking solution is absorbed by an already swollen fiber, the fiber is in effect "dried" of water, but the fiber retains its preexisting partially swollen condition.

For describing the degree to which the fiber is swollen, it is useful to again refer to the fluid retention value (FRV) of the fiber subsequent to crosslinking. Fibers having higher FRV's correspond to fibers which have been crosslinked while in a more swollen state relative to fibers crosslinked while in a less swollen state, all other factors being equal. Without limiting the scope of the invention, it is believed that partially swollen, crosslinked fibers with increased FRV's have greater wet resilience and responsiveness to wetting than fibers which have been crosslinked while in an unswollen state. Fibers having this increase in wet resilience and responsiveness to wetting are more readily able to expand or untwist when wetted in an attempt to return to their natural state. Yet, due to the stiffness imparted by crosslinking, the fibers are still able to provide the structural support to a saturated pad made from the fibers. Numerical FRV data described herein in connection with partially swollen crosslinked fibers shall be water retention values (WRV). As the WRV increases beyond approximately 60, the stiffness of the fibers is believed to become insufficient to provide the wet resilience and responsiveness to wetting desired to support a saturated absorbent structure.

In an alternative method of crosslinking the fibers in solution, the fibers are first soaked in an aqueous or other fiber swelling solution, defluidized, dried to a desired level and subsequently submersed in a water-miscible crosslinking solution containing a catalyst and crosslinking agent as previously described. The fibers are preferably mechanically defibrated into fluff form subsequent to defluidization and prior to additional drying, in order to obtain the benefits of enhanced twist and curl as previously described. Mechanical defibration practiced subsequent to contacting the fibers with the crosslinking agent is less desirable, since such defibration would volatilize the crosslinking agent thus, possibly leading to atmospheric contamination by, or high air treatment investments due to, the crosslinking agent.

In a modification of the process described immediately above, the fibers are defibrated and then pre-soaked in a high concentration solution of crosslinking agent and a fiber-swelling diluent, preferably water. The crosslinking agent concentration is sufficiently high to inhibit water-induced swelling of fibers. Fifty percent, by weight, aqueous solutions of the crosslinking agents of this invention, preferably, glutaraldehyde, have been found to be useful solutions for presoaking the fibers. The presoaked fibers are defluidized and submerged in a crosslinking solution containing a water-miscible, polar diluent, a catalyst, and a limited amount of water, and then crosslinked as previously described. Also as described above, the crosslinked fibers may be defluidized and subjected to a second mechanical defibration step prior to further processing into a sheet or absorbent structure.

Presoaking the fibers with crosslinking agent in an aqueous solution prior to causing the crosslinking agent to react provides unexpectedly high absorbency properties for absorbent pads made from the crosslinked fibers, even relative to pads made from crosslinked fibers of the prior described nonaqueous solution cure processes wherein the fibers were not presoaked with a solution containing crosslinking agent.

The crosslinked fibers formed as a result of the preceding dry crosslinking and nonaqueous solution crosslinking processes are the product of the present invention. The crosslinked fibers of the present invention may be utilized directly to the manufacture of air laid absorbent cores. Additionally, due to their stiffened and resilient character, the crosslinked fibers may be wet laid into an uncompacted, low density sheet which, when subsequently dried, is directly useful without further mechanical processing as an absorbent core. The crosslinked fibers may also be wet laid as compacted pulp sheets for sale or transport to distant locations.

Once the individualized, crosslinked fibers are made, they may be dry laid and directly formed into absorbent structures, or wet laid and formed into absorbent structures or densified pulp sheets. The fibers of the present invention provide a variety of substantial performance advantages. However, it is difficult to form such fibers into a smooth, wet laid sheet by conventional wet sheet formation practices. This is because individualized, crosslinked fibers rapidly flocculate when in solution. Such flocculation may occur both in the headbox and upon deposition into the foraminous forming wire. Attempts to sheet individualized, crosslinked fibers by conventional pulp sheeting methods have been found to result in the formation of a plurality of clumps of flocculated fibers. This results from the stiff, twisted character of the fibers, a low level of fiber to fiber bonding, and the high drainability of the fibers once deposited on a sheet forming wire. It is therefore a significant commercial concern that a practicable process for sheeting individualized, crosslinked fibers be provided, whereby wet laid absorbent structures and densified pulp sheets for transit and subsequent defibration may be formed.

Accordingly, a novel process for sheeting individualized, crosslinked fibers which tend to flocculate in solution has been developed, wherein a slurry containing individualized, crosslinked fibers are initially deposited on a foraminous forming wire, such as a Fourdrinier wire in a manner similar to conventional pulp sheeting processes. However, due to the nature of individualized, crosslinked fibers, these fibers are deposited on the forming wire in a plurality of clumps of fibers. At least one stream of fluid, preferably water, is directed at the deposited, clumped fibers. Preferably, a series of showers are directed at the fibers deposited on the forming wire, wherein successive showers have decreasing volumetric flow rates. The showers should be of sufficient velocity such that the impact of the fluid against the fibers acts to inhibit the formation of flocculations of the fibers and to disperse flocculations of fibers which have already formed. The fiber setting step is preferably performed with a cylindrical screen, such as a dandy roll, or with another apparatus analogous in function which is or may become known in the art. Once set, the fibrous sheet may then be dried and optionally compacted as desired. The spacing of the showers will vary depending upon the particular rate of fiber floccing, line speed of the forming wire, drainage through the forming wire, number of showers, and velocity and flow rate through the showers. Preferably, the showers are close enough together so that substantial levels of floccing are not incurred.

In addition to inhibiting the formation of and dispersing flocculations of fibers, the fluid showered onto the fibers also compensates for the extremely fast drainage of individualized, crosslinked fibers, by providing additional liquid medium in which the fibers may be dispersed for subsequent sheet formation. The plurality of showers of decreasing volumetric flow rates facilitates a systematic net increase in slurry consistency while providing a repetitive dispersive and inhibiting effect upon flocculations of the fibers. This results in the formation of a relatively smooth and even deposition of fibers which are then promptly, i.e., before reflocculation, set into sheeted form by allowing the fluid to drain and pressing the fibers against the foraminous wire.

Relative to pulp sheets made from conventional, uncrosslinked cellulosic fibers, the pump sheets made from the crosslinked fibers of the present invention are more difficult to compress to conventional pulp sheet densities. Therefore, it may be desirable to combine crosslinked fibers with uncrosslinked fibers, such as those conventionally used in the manufacture of absorbent cores. Pulp sheets containing stiffened, crosslinked fibers preparably contain between about 5% and about 90% uncrosslinked, cellulosic fibers, based upon the total dry weight of the sheet, mixed with the individualized, crosslinked fibers. It is especially preferred to include between about 5% and about 30% of highly refined, uncrosslinked cellulosic fibers, based upon the total dry weight of the sheet. Such highly refined fibers are refined or beaten to a freeness level less than about 300 ml CSF, and more preferably less than about 100 ml CSF. The uncrosslinked fibers are preferably mixed with an aqueous slurry of the individualized, crosslinked fibers. This mixture may then be formed into a densified pulp sheet for subsequent defibration and formation into absorbent pads. The incorporation of the uncrosslinked fibers eases compression of the pulp sheet into a densified form, while imparting a surprisingly small loss in absorbency to the subsequently formed absorbent pads. The uncrosslinked fibers additionally increase the tensile strength of the pulp sheet and to absorbent pads made either from the pulp sheet or directly from the mixture of crosslinked and uncrosslinked fibers. Regardless of whether the blend of crosslinked and uncrosslinked fibers are first made into a pulp sheet and then formed into an absorbent pad or formed directly into an absorbent pad, the absorbent pad may be air-laid or wet-laid as previously described.

Sheets or webs made from the individualized, crosslinked fibers, or from mixtures also containing uncrosslinked fibers, will preferably have basis weights of less than about 800 g/m$^2$ and densities of less than about 0.60 g/cm$^3$. Although it is not intended to limit the scope of the invention, wet-laid sheets having basis weights between about 300 g/m$^2$ and about 600 g/cm$^3$ are especially contemplated for direct application as absorbent cores in disposable articles such as diapers, tampons, and other catamenial products. Structures having basis weights and densities higher than these levels are believed to be most useful for subsequent comminution and air-laying or wet-laying to form a lower density and basis weight structure which is more useful for absorbent applications. Although, such higher basis weight and density structures also exhibit surprisingly high absorptivity and responsiveness to wetting. Other applications contemplated for the fibers of the present invention include tissue sheets, wherein the density of such sheets may be less than 0.10 g/cc.

For product applications wherein the crosslinked fibers are disposed next to or in the vicinity of a person's skin, it is desirable to further process the fibers to remove excess, unreacted crosslinking agent. Preferably, the level of unreacted crosslinking agent is reduced to at least below about 0.03%, based on the dry weight of the cellulosic fibers. One series of treatments found to successfully remove excess crosslinking agent comprise, in sequence, washing the crosslinked fibers, allowing the fibers to soak in an aqueous solution for an appreciable time, screening the fibers, dewatering the fibers, e.g., by centrifuging, to a consistency of between about 40% and about 80%, mechanically defibrating the dewatered fibers as previously described and air drying the fibers. This process has been found to reduce residual free crosslinking agent content to between about 0.01% and about 0.15%.

In another method for reducing residual crosslinking agent, readily extractable crosslinking agent is removed by alkaline washes. Alkalinity may be introduced by basic compounds such as sodium hydroxide, or alternatively in the form of oxidizing agents such as those chemicals commonly utilized as bleaching agents, e.g., sodium hypochlorite, and amino-containing compounds, e.g., ammonium hydroxide, which hydrolyze hemiacetal bonds to form Schiff bases. The pH is preferably maintained at a level of at least pH 7 and more preferably at least about pH 9, to inhibit reversion of the acetal crosslink bond. It is preferred to induce decomposition of hemiacetal bonds, while being neutral towards acetal bonds. Therefore, those extracting agents which operate at highly alkaline conditions are preferred. Single wash treatments with 0.01N and 0.1N ammonium hydroxide concentrations were observed to reduce residuals content to between about 0.0008% and about 0.0023% for soaking periods of 30 minutes to two (2) hours. Minimal additional benefit is believed to incur for soaking times in excess of about 30 minutes and for ammonium hydroxide concentrations in excess of about 0.01N.

Both single stage oxidation and multiple stage oxidation were found to be effective methods of extracting residual crosslinking agent. Single stage washing with 0.1% available chlorine (av.Cl) to about 0.8% av.Cl, based upon the dry weight of the fibers, supplied in the form of sodium hypochlorite was observed to reduce residual crosslinking agent levels to between about 0.0015% and about 0.0025%.

In one novel approach to producing crosslinked, individualized fibers, the source fibers are subjected to a conventional multistage bleaching sequence, but at a midpoint during the sequence the bleach process is interrupted and, the fibers are crosslinked in accordance with the present invention. Subsequent to curing, the remainder of the bleaching sequence is completed. It has been found that acceptably low crosslinking agent residual levels of less than about 0.006% can be obtained in this manner. This method is believed to embody the preferred manner of producing crosslinked fibers, since the capital expense and processing inconvenience of additional washing and extraction equipment and additional process steps are avoided due to merger of the bleaching and residual reduction steps. The bleaching sequences practiced and the point of interruption in the sequences for crosslinking may vary widely, as will be evident to one of ordinary skill in the art, However, multi-stage bleaching sequences, wherein DEP* or DEH* stages follow crosslinking, have been found to provide desirable results. (*D - chlorine dioxide, E - caustic extraction, P - peroxide, H - sodium hypochlorite). The post-crosslinking bleaching sequence stages are preferably alkaline treatments performed at pH greater than about pH 7 and more preferably greater than about pH 9.

In addition to providing effective reduction of residual crosslinking agent, post-crosslinking alkaline treatments have been observed to facilitate the development of higher FRV (fluid retention value) fibers for equivalent levels of crosslinking. The higher FRV fibers have lower dry resilience, i.e., they are easier to densify while in a dry state, while retaining substantially the same wet resilience and moisture responsiveness as the otherwise equivalent fibers crosslinked subsequent to completion of bleaching. This was especially surprising considering that higher FRV heretofore resulted in reduced absorbency properties.

The crosslinked fibers herein described are useful for a variety of absorbent articles including, but not limited to, disposable diapers, catamenials, sanitary napkins, tampons, and bandages wherein each of said articles has an absorbent structure containing the individualized, crosslinked fibers described herein. For example, a disposable diaper or similar article having a liquid permeable topsheet, a liquid impermeable backsheet connected to the topsheet, and an absorbent structure containing individualized, crosslinked fibers is particularly contemplated. Such articles are described generally in U.S. Pat. No. 3,860,003, issued to Kenneth B. Buell on Jan. 14, 1975, hereby incorporated by reference into this disclosure.

Conventionally, absorbent cores for diapers and certain other catamenials are made from unstiffened, uncrosslinked cellulosic fibers, wherein the absorbent cores have dry densities of about 0.06 g/cc and about 0.12 g/cc. Upon wetting, the absorbent core normally displays a reduction in volume.

It has been found that the crosslinked fibers of the present invention can be used to make absorbent cores having substantially higher fluid absorbing properties including, but not limited to, absorbent capacity and wicking rate relative to equivalent density absorbent cores made from conventional, uncrosslinked fibers or prior known crosslinked fibers. Furthermore, these improved absorbency results may be obtained in conjunction with increased levels of wet resiliency. For absorbent cores having densities of between about 0.06 g/cc and about 0.15 g/cc which maintain substantially constant volume upon wetting, it is especially preferred to utilize crosslinked fibers having crosslinking levels of between about 2.0 mole % and about 2.5 mole % crosslinking agent, based upon a dry cellulose anhydroglucose molar basis. Absorbent cores made from such fibers have a desirable combination of structural integrity, i.e., resistance to compression, and wet resilience. The term wet resilience, in the present context, refers to the ability of a moistened pad to spring back towards its original shape and volume upon exposure to and release from compressional forces. Compared to cores made from untreated fibers, and prior known crosslinked fibers, the absorbent cores made from the fibers of the present invention will regain a substantially higher proportion of their original volumes upon release of wet compressional forces.

In another preferred embodiment, the individualized, crosslinked fibers are formed into either an air laid or wet laid (and subsequently dried)l absorbent core which is compressed to a dry density less than the equilibrium wet density of the pad. The equilibrium wet density is the density of the pad, calculated on a dry fiber basis when the pad is fully saturated with fluid. When fibers are formed into an absorbent core having a dry density less than the equilibrium wet density, upon wetting to saturation, the core will collapse to the equilibrium wet density. Alternatively, when fibers are formed into an absorbent core having a dry density greater than the equilibrium wet density, upon wetting to saturation, the core will expand to the equilibrium wet density. Pads made from the fibers of the present invention have equilibrium wet densities which are substantially lower than pads made from conventional, uncrosslinked fibers. The fibers of the present invention can be compressed to a density higher than the equilibrium to form a pad which, upon wetting, well expand, thereby increasing absorbent capacity to a degree significantly greater than obtained for uncrosslinked fibers.

Especially high absorbency properties, wet resilience, and responsiveness to wetting may be obtained for crosslinking levels of between about 0.75 mole % and about 1.25 mole %, calculated on a dry cellulose molar basis. Preferably, such fibers are formed into absorbent cores having dry densities greater than their equilibrium wet densities. Preferably, the absorbent cores are compressed to densities of between about 0.12 g/cc and about 0.6 g/cc, wherein the corresponding equilibrium wet density is less than the density of the dry, compressed core. Also, preferably, the absorbent cores are compressed to a density of between about 0.12 g/cc and about 0.40 g/cc, wherein the corresponding equilibrium wet densities are between about 0.08 g/cc and about 0.12 g/cc. Relative to crosslinked fibers having crosslinking levels of between 2.0 mole % and about 2.5 mole %, the former fibers are less stiff, thereby making them more suitable for compression to the higher density range. The former fibers also have higher responsiveness to wetting in that upon wetting they spring open at a faster rate and to a greater degree than do fibers having crosslinking levels within the 2.0 mole % to 2.5 mole % range, have higher wet resiliency, and retain almost as much absorbent capacity. It should be recognized, however, that absorbent structures within the higher density range can be made from crosslinked fibers within the higher crosslinking level range, as can lower density absorbent structures be made from crosslinked fibers having lower levels of crosslinking. Improved performance relative to prior known individualized, crosslinked fibers is believed to be obtained for all such structures.

While the foregoing discussion involves preferred embodiments for high and low density absorbent structures, it should be recognized that a variety of combinations of absorbent structure densities and crosslinking agent levels between the ranges disclosed herein will provide superior absorbency characteristics and absorbent structure integrity relative to conventional cellulosic fibers and prior known crosslinked fibers. Such embodiments are meant to be included within the scope of this invention.

Absorbent structures made from individualized, crosslinked fibers may additionally contain discrete particles of substantially water-insoluble, hydrogel-forming material. Hydrogel-forming materials are chemical compounds capable of absorbing fluids and retaining them under moderate pressures.

Suitable hydrogel-forming materials can be inorganic materials such as silica gels or organic compounds such as crosslinked polymers. It should be understood that crosslinking, when referred to in connection with hydrogel-forming materials, assumes a broader meaning than contemplated in connection with the reaction of crosslinking agents with cellulosic fibers to form individualized, crosslinked fibers. Crosslinked hydrogel-forming polymers may be crosslinked by covalent, ionic, vander Waals, or hydrogen bonding. Examples of hydrogel-forming materials include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogel-forming materials are those disclosed in Assarsson et al., U.S. Pat. No. 3,901.236, issued Aug. 26, 1975, the disclosure of which is incorporated herein by reference. Particularly preferred hydrogel-forming polymers for use in the absorbent core are hydrolyzed acrylonitrile grafted starch, acrylic acid grafted starch, polyacrylates, and isobutylene maleic anhydride copolymers or mixtures thereof. Examples of hydrogel-forming materials which may be used are Aqualic L-73, a partially neutralized polyacrylic acid made by Nippon Shokubai Co., Japan, and Sanwet IM 1000, a partially neutralized acrylic acid grafted starch made by Sanyo Co., Ltd., Japan. Hydrogel forming materials having relatively high gel strengths, as described in U.S. patent application Ser. No. 746,152, filed June 18, 1985, hereby incorporated herein by reference, are preferred for utilization with individualized, crosslinked fibers.

Process for preparing hydrogel-forming materials are disclosed in Masuda et al., U.S. Pat. No. 4,076,663, issued Feb. 28, 1978; in Tasubakimoto et al., U.S. Pat. No. 4,286,082, issued Aug. 25, 1981; and further in U.S. Pat. Nos. 3,734,876, 3,661,815, 3,670,731, 3,664,343, 3,783,871, and Belgian Patent No. 785,850, the disclosures of which are all incorporated herein by reference.

The hydrogel-forming material may be distributed throughout an absorbent structure containing individualized, crosslinked fibers, or be limited to distribution throughout a particular layer or section of the absorbent structure. In another embodiment, the hydrogel-forming material is adhered or laminated onto a sheet or film which is juxtaposed against a fibrous, absorbent structure, which may include individualized, crosslinked fibers. Such sheet or film may be multilayered such that the hydrogel-forming material is contained between the layers. In another embodiment, the hydrogel-forming material may be adhered directly onto the surface fibers of the absorbent structure.

Surprisingly large increases in skin dryness have been observed for absorbent structures combining the individualized, crosslinked fibers of the present invention and hydrogel-forming materials, according to the skin wetness level measured by an evaporimeter subsequent to contacting moistened absorbent structures to human skin. This improvement is believed due to the high wicking ability of individualized, crosslinked fibers relative to conventional fibers and the increased absorptive capacity of the structure. Unique wicking ability of structures made from individualized, crosslinked fibers results from the stiff nature of the fibers and the relatively large void spaced resulting therefrom. However, excessively high levels of crosslinking agent, as may be present in certain prior known individualized, crosslinked fibers, may reduce wicking due to the hydrophobic characteristics of the crosslinking agent.

Another important advantage has been observed with respect to absorbent structures made from individualized, crosslinked fibers having dry densities, which are higher than their corresponding equilibrium wet densities (calculated on a dry fiber basis). Specifically, this type of absorbent structure expands in volume upon wetting. As a result of this expansion, the interfiber capillary network of fibers also enlarges. In conventional absorbent structures having hydrogel-forming material blended therein, the hydrogel-forming material expands in volume due to fluid absorption, and may block or reduce in size the capillary routes for fluid absorption prior to utilization of the entire fluid absorbing potential of the structure. This phenomenon is known as gel blocking. Capillary enlargement due to expansion of fibrous network of the absorbent structure reduces the occurrence of gel blocking. This allows larger proportions of the fluid absorbency potential of the structure to be utilized and allows higher levels of hydrogel-forming material to be incorporated into the absorbent structure, without significant levels of gel-blocking, if desired.

Absorbent structures containing individualized, crosslinked fibers and hydrogel-forming material for diaper core applications preferably have dry densities of between about 0.15 g/cc and about 0.40 g/cc and preferably contain less than about 20% hydrogel-forming material, calculated on a dry fiber weight basis. Most preferably, the individualized, crosslinked fibers have between about 0.75 mole % and about 1.25 mole % glutaraldehyde, calculated on a cellulose anhydroglucose molar basis, reacted therewith in the form of intrafiber crosslink bonds wherein the fibers are formed into a relatively thin absorbent structure in a sufficiently compressed dry state such that the structure may expand upon wetting.

The hydrogel-forming material may be homogeneously dispersed throughout all or part of the absorbent structure. For a diaper structure as disclosed in U.S. Pat. No. 3,860,003 having an absorbent core which contains the preferred individualized, crosslinked fibers, has a dry density of about 0.20 g/cc, and also contains hydrogel-forming material dispersed throughout the core. It is presently believed that an optimal balance of diaper wicking, total absorbent capacity, skin wetness, and economic viability is obtained for Aqualic L-73 contents of between about 5 wt. % and about 20 wt. %, based on the total weight of the dry absorbent core. Between about 8 wt. % and about 10 wt. % of hydrogel-forming material such as Aqualic L-73 is preferably homogeneously blended with the individualized, crosslinked fiber-containing absorbent cores in products as disclosed in U.S. Pat. No. 3,860,003.

The absorbent structures described above may also include conventional, fluffed fibers, or highly refined fibers, wherein the amount of hydrogel-forming material is based upon the total weight of the fibers as previously discussed. The embodiments disclosed herein are exemplary in nature and are not meant to limit the scope of application of hydrogel-forming materials with individualized crosslinked fibers.

PROCEDURE FOR DETERMINING FLUID RETENTION VALUE

The following procedure was utilized to determine the water retention value of cellulosic fibers.

A sample of about 0.3 g to about 0.4 g of fibers is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value is calculated as follows:

$$WRV = \frac{(W - D)}{D} \times 100 \qquad (1)$$

where,
W = wet weight of the centrifuged fibers;
D = dry weight of the fibers; and
W-D = weight of absorbed water.

PROCEDURE FOR DETERMINING DRIP CAPACITY

The following procedure was utilized to determine drip capacity of absorbent cores. Drip capacity was utilized as a combined measure of absorbent capacity and absorbency rate of the cores.

A four inch by four inch absorbent pad weighing about 7.5 g is placed on a screen mesh. Synthetic urine is applied to the center of the pad at a rate of 8 ml/s. The flow of synthetic urine is halted when the first drop of synthetic urine escapes from the bottom or sides of the pad. The drip capacity is calculated by the difference in mass of the pad prior to and subsequent to introduction of the synthetic urine divided by the mass of the fibers, bone dry basis.

PROCEDURE FOR DETERMINING WET COMPRESSIBILITY

The following procedure was utilized to determine wet compressibility of absorbent structures. Wet compressibility was utilized as a measure of resistance to wet compression, wet structural integrity and wet resilience of the absorbent cores.

A four inch by four inch square pad weighing 7.5 g is prepared, its thickness measured and density calculated. The pad is loaded with synthetic urine to ten times its dry weight or to its saturation point, whichever is less. A 0.1 PSI compressional load is applied to the pad. After about 60 seconds, during which time the pad equilibrates, the thickness of the pad is measured. The compressional load is then increased to 1.1 PSI, the pad is allowed to equilibrate, and the thickness is measured. The compressional load is then reduced to 0.1 PSI, the pad allowed to equilibrate and the thickness is again measured. The densities are calculated for the pad at the original 0.1 PSI load, the 1.1 PSI load and the second 0.1 PSI load, referred to as 0.1 PSIR (PSI rebound) load. The void volume reported on cc/g, is then determined for each respective pressure load. The void volume is the reciprocal of the wet pad density minus the fiber volume (0.95 cc/g). The 0.1 PSI and 1.1 PSI void volumes are useful indicators of resistance to wet compression and wet structural integrity. Higher void volumes for a common initial pad densities indicate greater resistance to wet compression and greater wet structural integrity. The difference between 0.1 PSI and 0.1 PSIR void volumes is useful for comparing wet resilience of absorbent pads. A smaller difference between 0.1 PSI void volume and 0.1 PSIR void volume indicates higher wet resilience.

Also, the difference in caliper between the dry pad and the saturated pad prior to compression was found to be a useful indicator of the responsiveness of wetting of the pads.

PROCEDURE FOR DETERMINING DRY COMPRESSIBILITY

The following procedure was utilized to determine dry compressibility of absorbent cores. Dry compressibility was utilized as a measure of dry resilience of the cores.

A four inch by four inch square air laid pad having a mass of about 7.5 is prepared and compressed, in a dry state, by a hydraulic press to a pressure of 5500 lbs/16 in². The pad is inverted and the pressing is repeated. The thickness of the pad is measured before and after pressing with a no-load caliper. Density before and after pressing is then calculated as mass/(area X thickness). Larger differences between density before and after pressing indicate lower dry resilience.

PROCEDURE FOR DETERMINING LEVEL OF GLUTARALDEHYDE REACTED WITH CELLULOSIC FIBERS

The following procedure was utilized to determine the level of glutaraldehyde which reacted to form intrafiber crosslink bonds with the cellulosic component of the individualized, glutaraldehyde- crosslinked fibers.

A sample of individualized, crosslinked fibers is extracted with 0.1N HCl. The extract is separated from the fibers, and the same extraction/separation procedure is then repeated for each sample an additional three times. The extract from each extraction is separately mixed with an aqueous solution of 2,4-dinitrophenylhydrazone (DNPH). The reaction is allowed to proceed for 15 minutes after which a volume of chloroform is added to the mixture. The reaction mixture is mixed for an additional 45 minutes. The chloroform and aqueous layers are separated with a separatory funnel. The level of glutaraldehyde is determined by analyzing the chloroform layer by high pressure liquid chromatography (HPLC) for DNPH derivative.

The chromatographic conditions for HPLC analysis utilized were—Column: C-18 reversed phase; Detector: UV at 360 mm; Mobile phase 80:20 methanol: water; Flow rate: 1 ml/min.; measurement made: peak height. A calibration curve of peak height and glutaraldehyde content was developed by measuring the HPLC peak heights of five standard solutions having known levels of glutaraldehyde between 0 and 25 ppm.

Each of the four chloroform phases for each fiber sample was analyzed by HPLC, the peak height measured, and the corresponding level of glutaraldehyde determined from the calibration curve. The glutaraldehyde concentrations for each extraction were then summed and divided by the fiber sample weight (dry fiber basis) to provide glutaraldehyde content on a fibers weight basis.

Two glutaraldehyde peaks were present for each of the HPLC chromatograms. Either peak may be used, so long as that same peak is used throughout the procedure.

EXAMPLE 1

This example shows the effect of varying levels of a crosslinking agent, glutaraldehyde, on the absorbency and resiliency of absorbent pads made from individualized, crosslinked fibers. The individualized, crosslinked fibers were made by a dry crosslinking process.

For each sample, a quantity of never dried, southern softwood kraft (SSK) pulp were provided. The fibers had a moisture content of about 62.4% (equivalent to 37.6% consistency). A slurry was formed by adding the fibers to a solution containing a selected amount of 50% aqueous solution of glutaraldehyde, 30% (based upon the weight of the glutaraldehyde) zinc nitrate hexahydrate, demineralized water and a sufficient amount of 1N HCl to decrease the slurry pH to about 3.7. The fibers were soaked in the slurry for a period of 20 minutes and then dewatered to a fiber consistency of about 34% to about 35% by centrifuging. Next, the dewatered fibers were air dried to a fiber consistency of about 55% to about 56% with a blow through dryer utilizing ambient temperature air. The air dried fibers were defibrated utilizing a three-stage fluffing device as described in U.S. Pat. No. 3,987,968. The defibrated fibers were placed in trays and cured at 145° C. in an essentially static drying oven for a period of 45 minutes. Crosslinking was completed during the period in the oven. The crosslinked, individualized fibers were placed on a mesh screen and washed with about 20° C. water, soaked at 1% consistency for one (1) hour in 60° C. water, screened, washed with about 20° C. water for a second time, centrifuged to 60% fiber consistency, defibrated in a three stage fluffer as previously described, and dried to completion in a static drying oven at 105° C. for four (4) hours. The dried fibers were air laid to form absorbent pads. The pads were compressed with a hydraulic press to a density of 0.10 g/cc. The pads were tested for absorbency, resiliency, and amount of glutaraldehyde reacted according to the procedures herein defined. Glutaraldehyde reacted is reported in mole % calculated on a dry fiber cellulose anhydroglucose basis. The results are reported in Table 1.

TABLE 1

| Sample # | Glutaraldehyde (mole %) Added/Reacted | WRV (%) | Drip Cap. @ 8 ml/s (g/g) | Wet Compressibility (cc/g) | | |
|---|---|---|---|---|---|---|
| | | | | 0.1 PSI | 1.1 PSI | 0.1 PSIR |
| 1 | 0/0 | 79.2 | N/A | 10.68 | 6.04 | 6.46 |
| 2 | 1.73/0.44 | 51.0 | 6.98 | 11.25 | 5.72 | 6.57 |
| 3* | N/A/0.50 | 48.3 | N/A | N/A | N/A | N/A |
| 4 | 2.09/0.62 | 46.7 | N/A | 11.25 | 6.05 | 6.09 |
| 5 | 3.16/0.99 | 36.3 | 15.72 | 12.04 | 6.09 | 6.86 |
| 6 | 4.15/1.54 | 35.0 | 15.46 | 13.34 | 6.86 | 8.22 |
| 7 | 6.46/1.99 | 32.8 | 12.87 | 13.34 | 6.93 | 8.31 |
| 8 | 8.42/2.75 | 33.2 | 16.95 | 13.13 | 7.38 | 8.67 |
| 9 | 8.89/2.32 | 29.2 | 13.59 | 12.56 | 6.51 | 7.90 |
| 10 | 12.60/3.32 | 27.7 | 13.47 | 12.04 | 6.63 | 7.82 |

*Taken from a separate sample of fibers.
(N/A)—Not Available

EXAMPLE 2

The individualized, crosslinked fibers of Example 1 were formed into dry laid absorbent pads having a dry fiber density of 0.20g/cc. The pads were allowed to expand under unrestrained conditions upon wetting with synthetic urine during execution of the drip capacity procedure. The pads were subsequently tested for absorbency resiliency and structural integrity according to the previously outlined wet compressibility procedure. The results are reported in Table 2. Drip capacity and wet compressibility increased significantly at 0.50 mole % glutaraldehyde.

TABLE 2

| Sample # | Drip Capacity @ 8 ml/s (g/g) | Wet Compressibility (cc/g) | | |
|---|---|---|---|---|
| | | 0.1 PSI | 1.1 PSI | 0.1 PSIR |
| 1 | 4.56 | 8.95 | 5.38 | 5.90 |
| 2 | 7.84 | 8.31 | 4.80 | 5.72 |
| 3* | 11.05 | 11.71 | 6.63 | 7.31 |
| 4 | 9.65 | 8.90 | 5.11 | 6.10 |
| 5 | 12.23 | 11.87 | 6.35 | 7.52 |
| 6 | 13.37 | 10.54 | 6.04 | 7.25 |
| 7 | 11.09 | 9.80 | 5.67 | 6.92 |

TABLE 2-continued

| Sample # | Drip Capacity @ 8 ml/s (g/g) | Wet Compressibility (cc/g) | | |
|---|---|---|---|---|
| | | 0.1 PSI | 1.1 PSI | 0.1 PSIR |
| 8 | 12.04 | 9.69 | 5.72 | 6.86 |
| 9 | 7.99 | 9.80 | 5.50 | 6.74 |
| 10 | 3.57 | 9.25 | 5.50 | 6.46 |

*Taken from a separate sample of fibers.

EXAMPLE 3

The purpose of this example is to show that low levels of extractable crosslinking agent may be obtained by subjecting the fibers to bleaching sequence steps subsequent to crosslinking. The level of extractable crosslinking agent was determined by soaking a sample of the fibers in 40° C. deionized water at 2.5% consistency for one (1) hour. The glutaraldehyde extracted by glutaraldehyde on a dry fiber weight basis. The fibers were crosslinked by a dry crosslinking process.

Southern softwood kraft pulp (SSK) was provided. The pulp fibers were partially bleached by the following bleaching sequence stages: chlorination (C) - 3-4% consistency slurry treated with about 5% available chlorine (av. Cl) at about pH 2.5 and about 38° C. for 30 minutes; caustic extraction - 12% consistency slurry treated with 1.4 g/l NaOH at about 74° C. for 60 minutes; and hypochlorite treatment (H) - 12% consistency slurry treated with sufficient sodium hypochlorite, at 11-11.5 pH between 38° C. and 60° C. for 60 minutes, to provide a 60-65 Elretho brightness and a 15.5-16.5 cp viscosity. The partially bleached fibers were processed into individualized, crosslinked fibers utilizing glutaraldehyde as the crosslinking agent in accordance with the process described in Example 1. The fibers retained 2.29 mole % glutaraldehyde, calculated on a dry fiber cellulosic anhydroglucose molar basis. Typically, such fibers have extractable glutaraldehyde levels of about 1000 ppm (0.1%).

Bleaching of the partially bleached, individualized fibers was then continued and completed with a chlorine dioxide (D), extraction (E), and sodium hypochlorite (H) sequence (DEH). In the chlorine dioxide stage (D), individualized, crosslinked fibers were soaked in a 10% consistency aqueous slurry also containing a sufficient amount of sodium chlorite to provide 2% available chlorine on a dry fiber weight basis. After mixing, the pH of the slurry was reduced to about pH 2.5 by addition of HCl and then increased to pH 4.4 by addition of NaOH. The pulp slurry was next placed in a 70° C. oven for 2.5 hours, screened, rinsed with water to neutral pH and centrifuged to 61.4% consistency.

In the extraction stage, a 10% consistency aqueous slurry of the dewatered fibers were treated with 0.33 g NaOH/liter water for 1.5 hours in a 40° C. The fibers were then screened, rinsed with water to neutral pH and centrifuged to 62.4% consistency.

Finally, for the sodium hypochlorite stage (H), a 10% consistency slurry of the fibers containing sufficient sodium hypochlorite to provide 1.5% available chlorine on a dry fiber weight basis was prepared. The slurry was mixed and heated in 50° C. oven for one (1) hour. The fibers were then screened, rinsed to pH 5.0 and centrifuged to 62.4% consistency. The dewatered fibers were air dried, fluffed and dried to completion in a 105° C. oven for one (1) hour. The level of extractable glutaraldehyde of the fully bleached, individualized, crosslinked fibers was 5 ppm (0.0025%). This is well below the maximum level of extractable glutaraldehyde believed to be acceptable for applications wherein the fibers are utilized in proximity to human skin.

Also, it was found that pads made from the fibers which were partially bleached, crosslinked and then bleached to completion had unexpectedly higher fluid retention value and wicking rate and at least equivalent drip capacity and wet resilience as individualized fibers which were crosslinked subsequent to being fully bleached. However, as a result of the higher WRV, the fibers crosslinked at an intermediate point of the bleaching sequence were more compressible in a dry state.

Substantially equivalent results were obtained when a peroxide bleaching state (P) was substituted for the final hypochlorite stage (H). In the P stage, a 10% consistency slurry was treated with 0.5% hydrogen peroxide, fiber weight basis, at 11-11.5 pH and 08° C. for 90 minutes.

EXAMPLE 4

This example shows the effect of mixing an organic acid with an inorganic salt catalyst on the level of crosslinking reaction completion. The fibers were crosslinked by a dry crosslinking process.

A first sample of individualized, crosslinked fibers was prepared as described in Example 1, wherein 4.0 mole % glutaraldehyde was retained subsequent to dewatering. Analytical measurements of the fibers subsequent to crosslinking indicated that the level of glutaraldehyde reacted on the fibers was 1.58 mole %, corresponding to a reaction completion percentage of about 37%.

A second sample of individualized, crosslinked fibers was prepared the same way as the first sample described in this example, except that in addition to the zinc nitrate catalyst, a quantity of citric acid equivalent to 10 wt. % of the glutaraldehyde mixed with the zinc nitrate in the pulp slurry as an additional catalyst. Analytical measurements of the fibers subsequent to crosslinking indicated that the level of glutaraldehyde reacted on the fibers was 2.5 mole %, corresponding to a reaction completion percentage of about 61%, (molar basis) a 55.1% increase in reaction completion relative to the unmixed zinc nitrate catalyst sample.

EXAMPLE 5

This example disclosed the use of low levels of glyoxylic acid, a dialdehyde acid analogue having one aldehyde group, in a dry crosslinking process as described in Example 1.

A fibrous slurry of never dried SSK containing a sufficient amount of glyoxylic acid to provide an estimated 1.2% glyoxylic acid reacted with cellulosic fibers, on a cellulose anhydroglucose molar basis and a zinc nitrate hexahydrate catalyst was prepared. The centrifuged fibers had a fiber consistency of about 38% and contained about 1.06 wt % glyoxylic acid, on a dry fiber basis. The catalyst to crosslinking agent ratio was about 0.30. The pH of the slurry at the start of crosslinking was about 2.16. The fibers were individualized and crosslinked according to the procedures described in Example 1.

In a second sample about 0.53 wt % glyoxylic acid, based on a dry fiber weight basis, was added to the fibers to provide an estimated level of glyoxylic acid reacted with the fibers of about 0.5 mole %, calculated on a cellulose anhydroglucose molar basis. The individualized, crosslinked fibers were otherwise prepared in accordance with the sample described immediately above, except that the slurry pH at the start of crosslinking was about 2.35.

Absorbent structures of 0.1 g/cc acid 0.2 g/cc densities were made from the individualized, crosslinked fibers as described in Example 2. The drip capacities, the wet compressibilities at 0.1 PSI, 1.1 PSI and 0.1 PSIR, and the wicking of the pads were significantly greater than for similar density absorbent structures made from conventional, uncrosslinked fibers.

EXAMPLE 6

This example discloses a method for making individualized, crosslinked fibers by a nonaqueous solution cure crosslinking process, wherein the fibers are crosslinked in a substantially nonswollen, collapsed state.

Never dried, SSK bleached fibers are provided and dried to fiber weight consistency of about 67%. The fibers are mechanically defibrated utilizing a three-stage fluffing device as described in U.S. Pat. No. 3,987,968. The defibrated fibers are then dried to completion at 105° C. for a period of four (4) hours. The dried fibers are next placed in a 10% consistency slurry of fibers and crosslinking solution, wherein the crosslinking solution contains between about 0.5 wt % and about 6.0 wt % of 50% glutaraldehyde solution, an additional quantity of water of between about 1.5 wt % and about 13 wt %, between about 0.3 wt % and about 3.0 wt % acid catalyst (HCl or $H_2SO_4$), and a balance of acetic acid. The fibers are maintained in the crosslinking solution for a period ranging between 0.5 hours and 6 hours, at a temperature of about 25° C., during which time the primarily intrafiber crosslink bonds are formed. The fibers are then washed with cold water and centrifuged to a fiber consistency of between about 60 wt % and about 65 wt %, defibrated with a three-stage fluffer and dried to 105° C. for a period of four hours. Such fibers will generally have between about 0.5 mole % and about 3.5 mole % crosslinking agent, calculated on a cellulose anhydroglucose molar basis, reacted therein. The dried fibers may be air laid to form absorbent structures and compressed to a density of 0.10 g/cc or 0.20 g/cc with a hydraulic press, similar to the pads formed in Examples 1 and 2, or to another density as desired.

EXAMPLE 7

This example discloses a method for making individualized, crosslinked fibers by a nonaqueous solution cure crosslinking process, whereby the fibers are crosslinked in a partially, but not completely swollen condition.

The process followed is identical to that described in Example 6, except that the never dried SSK fibers initially are dried to a 50-55 wt % fiber consistency before defibration, and the defibrated fibers are dried to a moisture content of between about 18 wt % and about 30 wt % as a result of such defibration and, if required, an additional drying step. The fibers, which have a partially swollen configuration, are then crosslinked, washed, centrifuged, defibrated and dried as described in Example 6. Relative to the crosslinked fibers of Example 6, the partially swollen, crosslinked fibers of this example having substantially equivalent glutaraldehyde levels have higher WRV and make absorbent structures having higher drip capacity and wet compressibility.

EXAMPLE 8

This example discloses a method for making individualized, crosslinked fibers by a nonaqueous solution crosslinking process wherein the fibers are presoaked in a high concentration aqueous solution containing glutaraldehyde prior to crosslinking in a substantially nonaqueous crosslinking solution.

Never dried SSK fibers are mechanically separated by the defibration apparatus described in U.S. Pat. No. 3,987,968 and presoaked in an aqueous solution containing 50 wt % glutaraldehyde and 50 wt % water for a period of between about 2 minutes and about 30 minutes. The fibers are then mechanically pressed to provide partially swollen glutaraldehyde-impregnated fibers. The fibers are next crosslinked in the presence of a catalyst, washed, centrifuged, defibrated and dried as described in Example 6. Relative to crosslinked fibers of Examples 6 or 7 having equivalent levels of crosslinking, the fibers of the present example made absorbent structures having higher drip capacities and wet compressibilities.

EXAMPLE 9

Individualized, crosslinked fibers were prepared according to the process described in Example 7. The crosslinking solutions contained: 2% glutaraldehyde, 1.29% $H_2SO_4$, 3% water, balance acetic acid for Samples 1 and 2; and 0.5% glutaraldehyde, 0.6% $H_2SO_4$, 1.2% water, balance acetic acid for Samples 3 and 4. The moisture content of the fibers going into the crosslinking solution was 30% for samples 1 and 2, and 18% for samples 3 and 4. Glutaraldehyde reacted to form crosslink bonds with the fiber. WRV, drip capacity and wet compressibility rebound (0.1 PSIR) were measured and are reported below in Table 3.

TABLE 3

| Sample # | Fiber Moist. Cont. (%) | Glutar. Reacted (mole %) | Density (g/cc) | WRV (%) | Drip 8 ml/s (g/g) | Wet Compress. (cc/g) 0.1 PSIR |
|---|---|---|---|---|---|---|
| 1 | 30 | 3.2 | 0.10 | 55 | N/A | 8.4 |
| 2 | 30 | 3.2 | 0.20 | 55 | 14.4 | 7.7 |
| 3 | 18 | 1.6 | 0.10 | 46 | N/A | N/A |
| 4 | 18 | 1.6 | 0.20 | 46 | 12.6 | 7.2 |

(N/A) Not Available

EXAMPLE 10

The purpose of this example is to exemplify a process for making wet-laid sheets containing individualized, crosslinked fibers.

A 0.55% consistency slurry of a blend of fibers containing 90% individualized, crosslinked fibers made according to the process described in Example 1 and 10% conventional, uncrosslinked fibers having a freeness of less than 100 CSF were deposited in flocculated, clumped fibers on a conventional 84-mesh Fourdrinier forming wire. The papermaking flow rate out of the headbox was 430 kg/min. Immediately after deposition, a series of five streams of water of sequentially decreasing flow rates were directed upon the fibers. The five streams of water provided a cumulative flow ratio 85 kg water/kg bone dry (b.d.) fiber. The showers were all spaced within an approximately 1 meter long area parallel to the direction of travel of the forming wire. Each stream of water was showered onto the fibers through a linear series of ⅛" (3.2 mm) ID circular aperatures spaced ½" (12.7 mm) apart and extending across the width of the forming wire. The approximate percentage of flow, based upon the total flow rate, and velocity of flow through the aperatures for each of the showers was as follows: Shower 1–37% of total flow, 170 m/min.; Shower 2–36% of total flow, 165 m/mm.; Shower 3–13% of total flow 61 m/min.; Shower 4–9% of total flow, 41 m/min.; Shower 5–5% of total flow, 20 m/min. Immediately after the fifth shower, the fibers were set by treatment with a cylindrical, screened roll known in the art as a Dandy Roll. The Dandy Roll pressed the fibers, which at the time of setting were in a high consistency slurry form, against the forming wire to set the fibers to form of a wet sheet. The sheet was similar in appearance to conventional fibrous pulp sheets.

The scope of the invention is to be defined according to the following claims.

What is claimed is:

1. An absorbent structure comprising individualized, twisted and curled, crosslinked cellulosic fibers having between about 0.5 mole % and about 3.5 mole % crosslinking agent, calculated on a cellulosic anhydroglucose molar basis, reacted with said fibers in an intrafiber crosslink bond form, wherein said crosslinking agent is selected from the group consisting of $C_2$–$C_8$ dialdehydes, $C_2$–$C_8$ dialdehyde acid analogues having at least one aldehyde group, and oligomers of said aldehyde and dialdehyde acid analogues, said fibers having been maintained in substantially individual form during drying and crosslinking, said fibers having a WRV of from about 25 to about 60, and said fibers having the property of enabling said absorbent structure to have a wet equilibrium density less than its dry density, said wet equilibrium density being calculated on a dry fiber basis.

2. The absorbent structure of claim 1 wherein said fibers have between about 0.75 mole % and about 2.5 mole % crosslinking agent, calculated on a cellulose anhydroglucose molar basis, reacted therewith in the form of intrafiber crosslink bonds.

3. The absorbent structure of claim 1 wherein said crosslinking agent is selected from the group consisting of glutaraldehyde, glyoxal, and glyoxylic acid.

4. The absorbent structure of claim 3 wherein said crosslinking agent is glutaraldehyde.

5. The absorbent structure of claim 2 wherein said crosslinking agent is selected from the group consisting of glutaraldehyde, glyoxal, and glyoxylic acid.

6. The absorbent structure of claim 5 wherein said crosslinking agent is glutaraldehyde.

7. The absorbent structure of claim 2 wherein said WRV is between about 28 and about 45.

8. The absorbent structure of claim 3 wherein said WRV is between about 28 and about 45.

9. The absorbent structure of claim 6 wherein said WRV is between about 28 and about 45.

10. The absorbent structure of claim 1, 3, 5, 6, or 9 wherein said equilibrium wet density is less than said dry density.

11. The absorbent structure of claim 1 wherein said absorbent structure has a dry density of less than about 0.60 g/cc.

12. The absorbent structure of claim 5 wherein said absorbent structure has a dry density of less than about 0.60 g/cc.

13. The absorbent structure of claim 7 wherein said absorbent structure has a dry density of between about 0.06 g/cc and about 0.15 g/cc and said individualized, crosslinked fibers have between about 2.0 mole % and about 2.5 mole % crosslinking agent, calculated on a cellulose anhydroglucose molar basis, reacted therewith in the form of intrafiber crosslink bonds.

14. The absorbent structure of claim 7 wherein said absorbent structure has a dry fiber density of between about 0.12 g/cc and about 0.60 g/cc and an equilibrium wet density, calculated on a dry fiber basis, which is less than said actual dry fiber density, and said individualized, crosslinked fibers have between about 0.75 mole % and about 1.25 mole % crosslinking agent, calculated on a cellulose anhydroglucose molar basis, reacted therewith in the form of intrafiber crosslink bonds.

15. The absorbent structure of claim 1 wherein said structure comprises between about 10% and about 95% individualized crosslinked fibers, and between about 5% and about 90% uncrosslinked cellulosic fibers.

16. The absorbent structure of claim 15 wherein said uncrosslinked, cellulosic fibers have a Canadian Standard Freeness of less than about 300.

17. The absorbent structure of claim 1 further comprising a hydrogel-forming material disposed upon said fibers.

18. The absorbent structure of claim 17 wherein said hydrogel-forming material is substantially homogeneously blended throughout as least part of said absorbent structure.

19. The absorbent structure of claim 1 wherein said hydrogel-forming material is disposed upon a sheet, said sheet being juxtaposed against said fibers.

20. The absorbent structure of claim 15 further comprising a hydrogel-forming material disposed upon said fibers.

21. The absorbent structure of claim 16 further comprising a hydrogel-forming material disposed upon said fibers.

22. The absorbent structure of claim 13 or 14 further comprising a hydrogel-forming material disposed within said absorbent structure.

23. The absorbent structure of claim 20 further comprising a hydrogel-forming material disposed within said absorbent structure.

24. The absorbent structure of claim 21 further comprising a hydrogel-forming material disposed within said absorbent structure.

25. A disposable absorbent article comprising a topsheet, a backsheet connected to said topsheet, and an absorbent structure as recited in claim 1, 11, 13, 14, 15, 16, 17, 18, 19, 23, or 24 disposed between said topsheet and said backsheet.

26. The absorbent structure of claim 1, 2, 3, 4, or 5 wherein said absorbent structure has a basis weight of less than about 800 g/m$^2$, and a dry density of less than about 0.60 g/cc.

27. The absorbent structure of claim 1 further comprising hydrogel-forming material disposed within said structure.

28. The absorbent structure of claim 27 wherein said hydrogel-forming material is substantially homogeneously blended throughout at least a part of said absorbent structure.

29. The absorbent structure of claim 27 wherein said hydrogel-forming material is disposed upon a sheet, said sheet being juxtaposed against said fibers.

30. The absorbent structure of claim 20 or 21, wherein said absorbent structure has a dry density of between about 0.06 g/cc and about 0.15 g/cc, and said individualized crosslinked fibers have between about 2.0 mole % and about 2.5 mole % crosslinking agent, calculated on a cellulose anhydroglucose molar basis, reacted therewith in the from of intrafiber crosslink bonds.

31. The absorbent structure of claim 20 or 21, wherein said absorbent structure has a dry density of between about 0.12 g/cc and about 0.60 g/cc, and an equilibrium wet density, calculated on a dry fiber basis, which is less than said dry density, and said individualized crosslinked fibers have between about 0.75 mole % and about 1.25 mole % crosslinking agent, calculated on a cellulose anhydroglucose molar basis, reacted therewith in the form of intrafiber crosslink bonds.

32. The absorbent structure of claim 20 or 21 wherein said absorbent structure has a dry density and an equilibrium wet density, calculated on a dry fiber basis, said equilibrium wet density being less than said dry density.

* * * * *

UNITED STATES PATENT AND TRADEMARK OFFICE
CERTIFICATE OF CORRECTION

PATENT NO. : 4,822,453         Page 1 of 4

DATED     : April 18, 1989

INVENTOR(S) : Walter L. Dean, Danny R. Moore, James W. Owens, Howard L. Schoggen It is certified that error appears in the above-identified patent and that said Letters Patent is hereby corrected as shown below:

Column 1, line 17, reads "fibers" should read --fibers,--.

Column 1, line 20, reads "of single" should read --of a single--.

Column 1, line 30, reads "individualizes" should read --individualized--.

Column 2, line 11 reads "3,421,553" should read --3,241,553--.

Column 2, line 11, reads "Steiger Mar." should read --Steiger on Mar.--.

Column 2, line 20, reads "3,421,553" should read --3,241,553--.

Column 2, line 24, reads "resilient" should read --resilience--.

Column 3, line 23, reads "form" should read --from--.

Column 3, line 31, reads "form" should read --from--.

Column 3, line 57, reads "med" should read --met--.

Column 3, line 61, reads "2.5" should read --3.5--.

Column 4, line 15, reads "absorbent capacity and skin dryness of" should read --absorbent capacity of--.

UNITED STATES PATENT AND TRADEMARK OFFICE
CERTIFICATE OF CORRECTION

PATENT NO. : 4,822,453

DATED : April 18, 1989

INVENTOR(S) : Walter L. Dean, Danny R. Moore, James W. Owens, Howard L. Schoggen It is certified that error appears in the above-identified patent and that said Letters Patent is hereby corrected as shown below:

Column 5, line 16, reads "reached," should read --reacted,--.

Column 5, line 34, reads "penetrated" should read --penetrates--.

Column 5, line 53, reads "result sin" should read --results in--.

Column 5, line 65, reads "if favored" should read --is favored--.

Column 6, line 2, reads "density individualized" should read --density, individualized,--.

Column 6, line 10, reads "defibration" should read --defribrating--.

Column 7, line 15, reads "defibrating the" should read --defibrating, the--.

Column 7, line 65, reads "catalyst" should read --catalysts--.

Column 7, line 68, reads "chlorides nitrates" should read --chlorides, nitrates--.

Column 10, line 27, reads "moles 5" should read --mole %--.

UNITED STATES PATENT AND TRADEMARK OFFICE
CERTIFICATE OF CORRECTION

PATENT NO. : 4,822,453

DATED : April 18, 1989

INVENTOR(S) : Walter L. Dean, Danny R. Moore, James W. Owens, Howard L. Schoggen It is certified that error appears in the above-identified patent and that said Letters Patent is hereby corrected as shown below:

Column 10, line 55, reads "include" should read --induce--.

Column 10, line 57, reads "however may" should read --however, may--.

Column 10, line 68, reads "acids organic" should read --acids, organic--.

Column 11, line 61, reads "Both a" should read --Both air--.

Column 14, line 60, reads "directly to" should read --directly in--.

Column 16, line 38, reads "600 g/cm$_3^3$" should read --600 g/m$^2$ and densities between about 0.15 g/cm$^3$ and about 0.30 g/cm$^3$--.

Column 19, line 1, reads "well" should read --will--.

Column 20, line 57, reads "densities which" should read --densities which--.

Column 21, line 48, reads "vidualized crosslinked" should read --vidualized, crosslinked--.

Column 25, line 19, reads "glutaraldehyde" should read --the water was measured by HPLC, and reported as extractable glutaraldehyde--.

UNITED STATES PATENT AND TRADEMARK OFFICE
CERTIFICATE OF CORRECTION

PATENT NO. : 4,822,453

DATED : April 18, 1989

INVENTOR(S) : Walter L. Dean, Danny R. Moore, James W. Owens, Howard L. Schoggen It is certified that error appears in the above-identified patent and that said Letters Patent is hereby corrected as shown below:

Column 25, line 68 reads "5 ppm" should read --25 ppm--.

Column 26, line 17, reads "08°" should read --80°--.

Column 26, line 42, reads "2.5" should read --2.45--.

Column 26, line 67, reads "0.5" should read --0.6--.

Column 27, line 52, reads "whereby" should read --wherein--.

Column 29, line 23, reads "cellulosic" should read --cellulose--.

Column 29, line 28, reads "aldehyde" should read --dialdehydes--.

Signed and Sealed this

Twenty-seventh Day of March, 1990

Attest:

JEFFREY M. SAMUELS

*Attesting Officer*  *Acting Commissioner of Patents and Trademarks*